United States Patent [19]

Kent

[11] 4,452,775

[45] Jun. 5, 1984

[54] CHOLESTEROL MATRIX DELIVERY SYSTEM FOR SUSTAINED RELEASE OF MACROMOLECULES

[75] Inventor: John S. Kent, Palo Alto, Calif.

[73] Assignee: Syntex (U.S.A.) Inc., Palo Alto, Calif.

[21] Appl. No.: 446,749

[22] Filed: Dec. 3, 1982

[51] Int. Cl.$^3$ .................... A61K 9/26; A61K 31/56; A61K 37/02; A61K 37/26

[52] U.S. Cl. ........................................ 424/19; 424/22; 424/28; 424/14; 424/177; 424/178; 424/179; 424/95

[58] Field of Search .................... 424/19–22, 424/38, 177, 178

[56] References Cited

U.S. PATENT DOCUMENTS

| | | | |
|---|---|---|---|
| 3,800,038 | 3/1974 | Rudel | 424/239 |
| 3,828,106 | 8/1974 | Rudel | 424/239 |
| 4,164,560 | 8/1979 | Folkman et al. | 424/22 |
| 4,180,560 | 12/1979 | Katz et al. | 424/21 |
| 4,244,949 | 1/1981 | Gupta | 424/243 |

OTHER PUBLICATIONS

Rudel C.A. 81 #29537p, (1974).
Joseph et al., C.A. 87 #141179y, (1977).
Misra C.A. 89 #135762h, (1978).
Beck et al., C.A. 90 #92364f, (1979).
Meyer et al., C.A. 91 #49927a, (1977).
Gupta C.A. 91 #128998n, (1979).
Gupta C.A. 94 #115055e, (1981).
Misra et al., C.A. 95 #192314m, (1981).
Bernabei C.A. 97 #150631y, (1982).
Pontani C.A. 98 #166811p, (1983).

*Primary Examiner*—Shep K. Rose
*Attorney, Agent, or Firm*—Ellen J. Buckles; Tom M. Moran; Alan M. Krubiner

[57] ABSTRACT

Delivery systems for releasing macromolecular active agents to a body site at a controlled rate for a prolonged period of time, comprising a cholesteric matrix permeable to passage of the macromolecular active agent by diffusion, are disclosed. The cholesteric matrix comprises cholesterol powder and cholesterol prills optionally in combination with a binding agent and a lubricating agent. The macromolecular active agent is dispersed throughout the matrix; macromolecules suitable for release from this delivery system have molecular weights of about 1300 to about 75,000 and are at least very slightly soluble in water.

21 Claims, No Drawings

CHOLESTEROL MATRIX DELIVERY SYSTEM FOR SUSTAINED RELEASE OF MACROMOLECULES

BACKGROUND OF THE INVENTION

This invention relates to a delivery system for delivering macromolecular active agents (molecular weight greater than about 1300) at a controlled rate for a prolonged period of time. More specifically, it relates to a cholesteric matrix permeable to the passage by diffusion of the macromolecular active agents contained therein.

Diffusional active agent delivery systems comprising an active agent dispersed in a matrix that is permeable to the active agent are well known. The active agent is released from such systems by diffusing through the matrix at a controlled rate in accordance with Fick's Law. In the majority of these systems, the matrix is a synthetic polymer. U.S. Pat. Nos. 3,903,880; 4,069,307; and 4,016,251 assigned to the Alza Corporation disclose active agent delivery systems comprising a matrix of an ethylene vinyl acetate copolymer, wherein the mechanism of release of the active agent is diffusion. Cholesterol has also been used to form diffusional matrix delivery systems. For example, Kincl, et al in "Sustained Release Hormonal Preparation," *ACTA Endocrinologica*, 64, 256–264 (1970) disclosed cholesterol pellet implants that released progesterone, and Kent, et al in "The Use of a Cholesterol Matrix Pellet Implant for Early Studies on the Prolonged Release in Animals of Agonist Analogues of Luteinizing Hormone-Releasing Hormone," 7th Int. Sump. Controlled Release of Bioactive Materials, Fort Lauderdale, Fla., 1980, disclosed the use of a cholesterol matrix similar to the matrix of this invention, for the delivery of luteinizing hormone releasing hormone (LHRH) analogues.

The polymeric matrix delivery systems and the monolithic cholesterol matrix delivery systems known in the art work well for the sustained delivery of small molecules such as steroids and most antibiotics. However, the use of diffusional matrices for prolonged delivery of active agents has heretofore been limited to agents of relatively low molecular weight. No diffusional matrix delivery system has previously been known which is suitable for the prolonged release of macromolecules, particularly those whose molecular weight exceeds about 1300. Matrix delivery systems have in fact heretofore proven incapable of delivering large molecules at useful rates, due to the extremely low diffusivity of these molecules in known matrix materials. A possible exception are the polymeric matrix delivery systems disclosed in U.S. Pat. No. 4,164,560 to Folkman and Langer. However, the systems of that patent do not appear to operate by simple diffusion, and have an extremely uneven release rate profile.

There is a need for a biocompatible delivery system capable of prolonged administration of macromolecules to an appropriate body site. The utility of a wide variety of the macromolecular active agents presently of interest for applications in medicine and animal husbandry, is diminished by their short biological half lives, and the consequent necessity of frequent administration. In addition, many of these compounds have extremely low oral activity, and must be administered by injection.

SUMMARY OF THE INVENTION

Accordingly, it is an object of this invention to provide novel and useful diffusional matrix delivery systems for administering a macromolecular active agent at a controlled rate to a body site. The invention resides in the composition of the matrix component, which is a combination of two forms of cholesterol, powder and prills, in a ratio chosen to achieve the desired release rate for the particular macromolecule to be delivered. Accordingly, a diffusional matrix delivery system of this invention comprises: (a) 90.0–99.9%, by weight, of a matrix composed of a combination of cholesterol prills, cholesterol powder, and effective amounts of a biocompatible binding agent and a biocompatible lubricating agent, in which is dispersed (b) 0.1–10.0%, by weight, of a macromolecular active agent, wherein the matrix contains a plurality of micropores which are substantially permeable to the passage by diffusion of the macromolecular active agent, and said active agent is at least very slightly water soluble.

Another aspect of the invention resides in a method of administering a pharmaceutically acceptable macromolecular active agent to an animal, which comprises placing an appropriately sized and shaped delivery system of the above description in a body site which is capable of making available its intracellular and/or extracellular fluid for transfer into the micropores of the system.

DETAILED DESCRIPTION OF THE INVENTION

The active agent delivery systems of this invention provide several important advantages over previously known delivery systems. The most important advantage, as discussed above, is the provision of a matrix system which operates by diffusion and is capable of controlled and prolonged release of macromolecules. Another important advantage of the claimed delivery systems is their capacity to provide a range of useful release rates for a wide variety of macromolecular active agents. The delivery systems are tailored to the particular active agent, and the rate of release is controlled by adjustment of the size and tortuosity of the micropores within the matrix. This selectivity of porosity and tortuosity parameters is accomplished by varying the size of the cholesterol prills and the relative proportions of cholesterol prills, cholesterol powder, and binder, within the matrix.

The term "matrix", as used herein, denotes a solid phase carrier within which particles of active agent are dispersed. The carrier can be in any desired shape, such as sphere, spheroid, cylinder, and the like.

The term "very slightly soluble", as used herein, refers to a solubility of 0.1–1.0 mg/ml, as defined in the USP XX Reference Table at page 1121.

The abbreviation "m.w.", as used herein, refers to the molecular weight of the modified molecule.

The invention herein resides in the creation of a matrix formed of "pores" or channels, of such size and tortuosity as to permit the passage by diffusion at a controlled rate, of macromolecular active agents dispersed therein.

The system releases its active agent when placed at a body site which can make available its intracellular and/or extracellular fluid for transfer into the matrix. The fluid adjacent to the system enters the system through the intragranular spaces or pores. The active agent then dissolves into the permeating fluid phase and diffuses from the matrix, through the extracting biological fluid in the pores.

The matrix is composed of a combination of cholesterol powder and cholesterol prills, a biocompatible binding agent and, optionally, a biocompatible lubricating agent. The cholesterol powder is readily commercially available. The cholesterol prills are known and are available from the Southwest Research Institute, San Antonio, Tex. The prills can be made by a hot melt centrifugal extrusion process such as that described by Sommerville and Goodwin in *Controlled Release Technologies, Methods, Theories and Applications*, Vol. II, Ch. 8, edited by A. F. Kydonieus. The process as described by Sommerville and Goodwin is modified to the extent that the opening in the extrusion nozzle is circular rather than anular, so that the resultant prills are not encapsulated.

The diameter of the cholesterol prills can range from 100 to 1,200 microns. A preferred range is about 400 to about 700 microns.

The cholesterol powder and prills are combined with a binding agent, and optionally, a lubricating agent. The choice of binding and lubricating agents which may be effectively used to practice this invention is limited by the requirement that these agents be biocompatible. That is, the materials must be non-toxic to the host.

A number of binders and lubricating agents are known which meet these criteria. The binding agent used may be chosen from among, for example, the U.S.P. grade polyethylene glycols having molecular weights between 1,250 (PEG 1250) and 8,000 (PEG 8000), polyvinylpyrollidone, hydroxymethylcellulose, hydroxypropylmethylcellulose, and the materials commercially known under the trademark Pluronic ™ with molecular weights between 3,800 Pluronic ™ L101) and 14,000 (Pluronic ™ F127). A preferred binding agent is PEG 6000. Depending on the method of manufacture, incorporation in the matrix of an effective amount of a lubricating agent may facilitate production. Suitable lubricants include for example, stearic acid, magnesium stearate, calcium stearate, or Sterotex ™. Preferred among these are stearic acid and 100,000. The choice of macromolecules which can be delivered in accordance with the practice of this invention is limited only by the requirement that they be at least very slightly soluble in a aqueous physiological media such as plasma, interstitial fluid, and the intra and extracellular fluids of the subcutaneous space. The term "very slightly soluble" refers to a water solubility of at least about 0.1–1.0 mg/ml, as defined hereinabove.

Exemplary macromolecules include among others, proteins, enzymes, polynucleotides, nucleoproteins, polysaccharides, glycoproteins, lipoproteins, polypeptides (particularly hormonally active polypeptides), and synthetic analogues of these molecules.

Among the hormonally active polypeptides suitable for use in the practice of this invention, the mammalian growth hormones are of particular interest herein. Growth hormones may be considered generally to be any substance which stimulates growth. The growth hormones of interest herein are those polypeptides secreted by the anterior pituitary gland which exert an influence on protein, carbohydrate and lipid metabolism and control the rate of skeletal and visceral growth. Generally, growth hormones are species specific polypeptides with molecular weights falling between 22,000 and 24,000. In several species, for example, humans and cattle, the growth hormone also possess some of the activities of lactogenic hormones.

Human Growth Hormone (hGH) has been isolated, crystallized and characterized as a homogenous protein containing 191 amino acid residues and having a molecular weight of 22,128. It is isolated from humans, alone or with a much larger molecule which is probably an association of the primary polypeptide with another as yet unspecified protein. There are at least 4 isohormones of the primary molecule.

The description of the exact amino acid content and sequence of hGH has undergone some revisions since the initial sequencing was carried out. At present hGh is described as being comprised of the following number and sequence of amino acids.

| | | | | | | | | HUMAN GROWTH HORMONE | | | | | | | | | | | | | | | | | | | | | |
|---|---|---|---|---|---|---|---|---|---|---|---|---|---|---|---|---|---|---|---|---|---|---|---|---|---|---|---|---|---|---|
| | | | | 5 | | | | | | 10 | | | | | 15 | | | | | 20 | | | | | 25 | | | | | 30 |
| 1 | F | P | T | I | P | L | S | R | L | F | D | N | A | M | L | R | A | H | R | L | H | Q | L | A | F | D | T | Y | Q | E |
| 31 | F | E | E | A | Y | I | P | K | E | Q | K | Y | S | F | L | Q | N | P | Q | T | S | L | C | F | S | E | S | I | P | T |
| 61 | P | S | N | R | E | E | T | Q | Q | K | S | N | L | Q | L | L | R | I | S | L | L | L | I | Q | S | W | L | E | P | V |
| 91 | Q | F | L | R | S | V | F | A | N | S | L | V | Y | G | A | S | N | S | D | V | Y | D | L | L | K | D | L | E | E | G |
| 121 | I | Q | T | L | M | G | R | L | E | D | G | S | P | R | T | G | Q | I | F | K | Q | T | Y | S | K | F | D | T | N | S |
| 151 | H | N | D | D | A | L | L | K | N | Y | G | L | L | Y | C | F | R | K | D | M | D | K | V | E | T | F | L | R | I | V |
| 181 | Q | C | R | S | V | E | G | S | C | G | F | | | | | | | | | | | | | | | | | | | | |

| | | COMPOSITION | | | | | |
|---|---|---|---|---|---|---|---|
| 7 | ALA A | 14 | GLN Q | 26 | LEU L | 18 | SER S |
| 11 | ARG R | 13 | GLU E | 9 | LYS K | 10 | THR T |
| 9 | ASN N | 8 | GLY G | 3 | MET M | 1 | TRP W |
| 11 | ASP D | 3 | HIS H | 13 | PHE F | 8 | TYR Y |
| 4 | CYS C | 8 | ILE I | 8 | PRO P | 7 | VAL V |

MOL. WT. = 22,128    NUMBER OF RESIDUES = 191 magnesium stearate. The foregoing lists of binders and lubricants are not intended to be exhaustive of the materials which are compatible with the scope and intention of this invention, but merely set out examples to illustrate the types of lubricants and binders which may be used.

The macromolecular active agents which may be incorporated in the matrix of this invention are biologically active molecules having molecular weights greater than about 1,300, preferably between 10,000 and 400,000, and most preferably between about 10,000 and Two disulfide bridges are present in this molecule, one linking residues 67 and 165 and a second linking residues 182 and 189. The amino acid sequence given above is also set out in the *Atlas of Protein Sequence and Structure*, Vol 5, Suppl. 3, p. S-50, Dayhoff, M. O., Schwartz, R. M., and Orcutt, B. C., (Dayoff, M. O. ed) (1973) National Biomedical Research Foundation, Washington, D.C.

A subsequent publication, by Martial, J. A., et al, in *Science*, 205:602–607 1979, sets out the complementary DNA nucleotide sequence for hGH. This DNA sequence predicts glutamine, asparagine, glutamine, glutamic acid, glutamine, aspartic acid, asparagine, and glutamine at positions 29, 47, 49, 74, 91, 107, 109 and 122 respectively, while degradative protein sequencing indicates glutamic acid, aspartic acid, glutamic acid, glutamine, glutamic acid, asparagine, aspartic acid, and glutamic acid at these positions.

Availability of hGH has until recently been limited to that which could be extracted from the pituitary gland of human cadavers. However, recombinant DNA techniques have made it possible recently to produce from bacteria biologically active hGH in relatively substantial quantities. See, for example, Martial, J. A. Baxter, J. D. and Hallewell, R. A., *Science*, 205:602–607, 1979.

Bovine Growth Hormone (bGH) has the same number of residues as hGH, 191, but there exist some differences in the amino acid residue sequence and in the numbers of particular residues. As set out in the *Atlas of Protein Sequence and Structure* identified above, bGH is comprised of the following sequence or amino acid residues:

| BOVINE GROWTH HORMONE | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | | | | 5 | | | | | 10 | | | | | 15 | | | | | 20 | | | | | 25 | | | | | 30 | |
| 1 | A | F | P | A | M | S | L | S | G | L | F | A | N | A | V | L | R | A | Q | H | L | H | Q | L | A | A | D | T | F | K |
| 31 | E | F | E | R | T | Y | I | P | E | G | Q | R | Y | S | I | Q | N | T | Q | V | A | F | C | F | S | E | T | I | P | A |
| 61 | P | T | G | K | N | E | A | Q | Q | K | S | D | L | E | L | L | R | I | S | L | L | L | I | Q | S | W | L | G | P | L |
| 91 | Q | F | L | S | R | V | F | T | N | S | L | V | F | G | T | S | D | R | V | Y | E | K | L | K | D | L | E | E | G | I |
| 121 | L | A | L | M | R | E | L | E | D | G | T | P | R | A | G | Q | I | L | K | Q | T | Y | D | K | F | D | T | N | M | R |
| 151 | S | D | D | A | L | L | K | N | Y | G | L | L | S | C | F | R | K | D | L | H | K | T | E | T | Y | L | R | V | M | K |
| 181 | C | R | R | F | G | E | A | S | C | A | R | | | | | | | | | | | | | | | | | | | | |

| COMPOSITION | | | | | | | |
|---|---|---|---|---|---|---|---|
| 15 | ALA A | 11 | GLN Q | 27 | LEU L | 13 | SER S |
| 13 | ARG R | 13 | GLU E | 11 | LYS K | 12 | THR T |
| 6 | ASN N | 10 | GLY G | 4 | MET M | 1 | TRP W |
| 10 | ASP D | 3 | HIS H | 13 | PHE F | 6 | TYR Y |
| 4 | CYS C | 7 | ILE I | 6 | PRO P | 6 | VAL V |

MOL. WT. = 21,816   NUMBER OF RESIDUES = 191

Molecular cloning of DNA complementary to bGH mRNA carried out by Miller, W. L., Martial, J. A., and Baster, (J. D., *J. of Biol. Chem.*, Vol. 255, No. 16, pp 7521–7524 (1980) confirms this sequence except at positions 47 and 66 where aspartic acid and glutamic acid are replaced by their respective amides.

The primary source of bGH is the pituitary glands of slaughtered cattle. Methods of obtaining such materials are known in the art, for example, see the W. L. Miller reference given above.

In addition this invention is to encompass the growth hormones of sheep and horses. The amino acid residue sequence of both these hormones has been reported in the *Atlas of Protein Sequence and Structure* as follows:

| SHEEP GROWTH HORMONE | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | | | | 5 | | | | | 10 | | | | | 15 | | | | | 20 | | | | | 25 | | | | | 30 | |
| 1 | A | F | P | A | M | S | L | S | G | L | F | A | N | A | V | L | R | A | Q | H | L | H | Q | L | A | A | D | T | F | K |
| 31 | E | F | E | R | T | Y | I | P | E | G | Q | R | Y | S | I | Q | N | T | Q | V | A | F | C | F | S | E | T | I | P | A |
| 61 | P | T | G | K | N | E | A | Q | Q | K | S | D | L | E | L | L | R | I | S | L | L | L | I | Q | S | W | L | G | P | L |
| 91 | Q | F | L | S | R | V | F | T | D | S | L | V | F | G | T | S | D | R | V | Y | E | K | L | K | D | L | E | E | G | I |
| 121 | L | A | L | M | R | E | L | E | D | V | T | P | R | A | G | Q | I | L | K | Q | T | Y | D | K | F | D | T | N | M | R |
| 151 | S | D | D | A | L | L | K | N | Y | G | L | L | S | C | F | R | K | D | L | H | K | T | E | T | Y | L | R | V | M | K |
| 181 | C | R | R | F | G | E | A | S | C | A | F | | | | | | | | | | | | | | | | | | | | |

| COMPOSITION | | | | | | | |
|---|---|---|---|---|---|---|---|
| 115 | ALA A | 11 | GLN Q | 27 | LEU L | 13 | SER S |
| 13 | ARG R | 13 | GLU E | 11 | LYS K | 12 | THR T |
| 5 | ASN N | 9 | Gly G | 4 | MET M | 1 | TRP W |
| 11 | ASP D | 3 | HIS H | 13 | PHE F | 6 | TYR Y |
| 4 | CYS C | 7 | ILE I | 6 | PRO P | 7 | VAL V |

MOL. WT. = 21,859   NUMBER OF RESIDUES = 191

| HORSE GROWTH HORMONE | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | | | | 5 | | | | | 10 | | | | | 15 | | | | | 20 | | | | | 25 | | | | | 30 | |
| 1 | F | P | A | M | P | L | S | S | L | F | A | N | A | V | L | R | A | Q | H | L | H | Q | L | A | A | D | T | Y | K | E |
| 31 | F | E | R | A | Y | I | P | E | G | Q | R | Y | S | I | Q | N | A | Q | A | A | F | C | F | S | E | T | I | P | A | P |
| 61 | T | G | K | D | E | A | Q | Q | R | S | D | M | E | L | L | R | F | S | L | L | L | I | Q | S | W | L | G | P | V | Q |
| 91 | L | L | S | R | V | F | T | N | S | L | V | F | G | T | S | D | R | V | Y | E | K | L | R | D | L | E | E | G | I | Q |
| 121 | A | L | M | R | E | L | E | D | G | S | P | R | A | G | Q | I | L | K | Q | T | Y | D | K | F | D | T | N | L | R | S |
| 151 | D | D | A | L | L | K | N | Y | G | L | L | S | C | F | K | K | D | L | H | K | A | E | T | Y | L | R | V | M | K | C |
| 181 | R | R | F | V | E | S | S | C | A | F | | | | | | | | | | | | | | | | | | | | | |

| COMPOSITION | | | | | | | |
|---|---|---|---|---|---|---|---|
| 17 | ALA A | 12 | GLN Q | 26 | LEU L | 15 | SER S |
| 14 | ARG R | 13 | GLU E | 10 | LYS K | 8 | THR T |
| 5 | ASN N | 8 | GLY G | 4 | MET M | 1 | TRP W |
| 11 | ASP D | 3 | HIS H | 12 | PHE F | 7 | TYR Y |
| 4 | CYS C | 6 | ILE I | 7 | PRO P | 7 | VAL V |

| MOL. WT. = 21,757 | NUMBER OF RESIDUES = 190 |
|---|---|

These two growth hormones are presently available from the pituitary gland of the respective animals and are obtained by methods known in the art as set out for example in W. L. Miller reference given above.

The invention herein also encompasses the controlled release of human pancreas growth hormone releasing factor (hpGRF). Human pancreas growth hormone releasing factor has been isolated and characterized as a 44 amino acid peptide composed of the following sequence of amino acids:

| HUMAN GROWTH HORMONE RELEASING FACTOR | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| | | | | 5 | | | | | 10 | | | | | 15 | | | | | 20 | | | | | 25 | | | | | 30 |
| 1 | Y | Q | D | A | I | F | T | N | S | Y | R | K | V | L | G | Q | L | S | A | R | R | L | L | Q | D | I | M | S | Q |
| 31 | Q | G | E | S | N | Q | E | R | G | A | R | A | R | L | | | | | | | | | | | | | | | |
| NUMBER OF RESIDUES = 44 | | | | | | | | | | | | | | | | | | | | | | | | | | | | | |

A more complete description of hpGRH, as well as methods of extracting and isolating the protein are given by R. Guillemin et al in *Science* 218:585–587 (1982), the contents of which are incorporated herein by reference. HpGRF can also be obtained by solid-phase synthesis techniques known in the art, and specifically described by N. Ling et al in *Biochem. Biophys. Les. Commun*, 95:945 (1980), the contents of which are incorporated herein by reference.

Other peptide hormones which are suitable for use in this invention include insulin (m.w. 6000), glucagon (m.w. 3500), thyroid stimulating hormone (m.w. 13,600–14,700), parathyroid and pituitary hormones, calcitonin (m.w. 4,500), renin, prolactin (m.w. 21,000), corticotrophin (m.w. 7,500), follicle stimulating hormone (m.w. 36,000) and chorionic gonadotrophin (m.w. 30,000–60,000). The molecular weights given for these peptides are approximate, and are reported in *Peptide Hormones*, Edited by Parsons, J. A., published by University Park Press, London, 1975.

Enzymes suitable for delivery in accordance with the practice of this invention include, for example, hydrolases, transferases, proteases, ligases, isomerases, lysases, and the oxidoreductases such as esterases, phoshophatases, glycosidases, and peptidases. These enzymes are described in *Enzymes*, edited by Dixon, M. and Webb, E. C., 1964, published by Academic Press Inc., New York. Also capable of delivery from the system of this invention are bovine serum albumin (m.w. 68,000), human serum albumin (m.w. 66,500), proalbumen, unsecreted adrenocorticotrophin (m.w. 35,000) thyroglobulin (m.w. 660,000), soybean trypsin inhibitor (m.w. 21,000), alkaline phosphatase (m.w. 88,000, and Gatalase (m.w. 250,000).

The lists of macromolecules recited above are given only to illustrate the types of active agents which are suitable for use in practicing the invention, and are not intended to be exhaustive.

The relative proportions of active agent and matrix components can be varied within defined ranges depending on the macromolecule to be administered and the desired rate and duration of release. The macromolecular active agent may comprise 0.1–10.0%, by weight, of the delivery system. The actual amount of active agent incorporated in the delivery system will depend on the particular active agent, the desired effect, and, to a limited extent, the desired duration of release; a preferred amount of active agent is 2 to 5%, by weight, of the system. The relative proportions of the matrix components may be varied within the following ranges:

(a) 20–80% cholesterol powder;
(b) 20–80% cholesterol prills, 100–1200 microns in diameter;
(c) 0.1–5.0% biocompatible binding agent;
(d) 0.1–5.0% biocompatible lubricating agent.

A preferred matrix composition comprises, by weight:

(a) 40–60% cholesterol powder;
(b) 40–60% cholesterol prills having diameters of 200–800 microns;
(c) 0.1–1.0% biocompatible binding agent; and
(d) 0.5–1.5% biocompatible lubricating agent.

An especially preferred matrix composition comprises, by weight:

(a) 48–52% cholesterol powder;
(b) 48–52% cholesterol prills having diameters of 420–710 microns;
(c) 0.4–0.6% biocompatible binding agent; and
(d) 0.8–1.0% biocompatible lubricating agent.

The size of the cholesterol prill may vary from about 100–1200 microns in diameter. A preferred range is about 400–700 microns.

The choices of matrix component proportions and cholesterol prill size are governed in large part by the macromolecule to be delivered, the desired release rate and duration of release, and the body site at which the system is to be placed. Those skilled in the art can readily determine the rate of diffusion of active agents through the cholesterol matrix when wetted by the biological fluids of the targeted body site, and adjust the ratios and sizes of matrix components to achieve a delivery system which is best suited to the particular active agent and site of prills, binder, lubricant and active agent for particular application.

The active agent delivery systems of this invention exhibit classic matrix diffusion kinetics for the release of macromolecules; i.e., the rate of release is dependent on time, proportional to time $\frac{1}{2}$. Thus, as described by Higuchi, *J. Pharm. Sci.*, 52,1145, the release rate profile of a given embodiment of this invention is governed by the relationship $$Q = \left[ \frac{D\epsilon}{\gamma} (2A - \epsilon C_s) C_s t \right]^{\frac{1}{2}} \qquad \text{I}$$

where Q is the amount of active agent released per unit surface area of the system, D is the diffusivity or diffusion coefficient of the active agent in the release medium (i.e. the biological fluid at the site of placement of the delivery system), $\epsilon$ is the porosity of the matrix, $\gamma$ is the tortuosity of the matrix, $C_s$ is the solubility of the drug in the release medium (as defined above for D), and A is the concentration of the active agent in the matrix, expressed as unit weight/unit volume.

The diffusion coefficient, D, of a macromolecule in the release medium, can be determined by measuring the rate of transport of the macromolecule from one chamber through a sintered glass filter of known pore size and thickness into another chamber. The apparatus for this procedure may be two flasks which are interconnected by a sintered glass filter. The pores of the filter should be greater in diameter than the macromolecular active agent. The method is carried out by adding to the first flask a measured amount of the biological release medium, or similar vehicle, while simultaneously adding to the second flask, equipped with a ground glass stopper and a stirring bar, the active agent in the same vehicle, such that the levels of liquid in the two flasks are approximately the same. The contents of the flasks are then stirred, and samples withdrawn from the downstream flask at predetermined intervals for analysis. The diffusion coefficient, D, is then calculated from the rate of change in concentration of active agent in the downstream chamber. This procedure is well known to the art, and is described in *J. Pharm. Sci.*, Vol. 55, pp. 1224 to 1229, 1966. Alternatively, the diffusion coefficient of an active agent macromolecule can be determined by the methods described in *Diffusion in Solids*, by W. Jost, Chapter XI, pages 436 to 488, 1960, Revised Edition, Academic Press Inc., New York.

The solubility of the active agent in the release medium or similar in vitro vehicle can be determined by any of the various standard techniques which are well known in the art. One method consists in placing in the vehicle or medium an amount of the active agent, which is in substantial excess of its solubility. The dissolution process is permitted to come to equilibrium, and the concentration of the active agent in solution is then measured. The flask or test tube in which the vehicle and active agent are placed can be immersed in a constant temperature waterbath, or covered with a temperature controlling sleeve, and should be shaken or stirred, for example with a Burrell wrist action shaker or a motor driven rotating spiral, for at least 24 hours. An aliquot of the vehicle is then filtered, and the filtrate analyzed for concentration of the active agent. Stirring is continued for an additional period of time, such as 24 hours, and a second aliquot of the vehicle is filtered and analyzed. If the concentration of active agent in the second aliquot is the same as the concentration in the first, equilibrium is presumed. If not, subsequent measurements are made at periodic intervals until equilibrium concentration is achieved. Analysis of the concentration of active agent in the vehicle can be accomplished by any suitable means, depending on the active agent. Many standard methods are well-known in the art, including, for example, spectrophotometric techniques (UV, visible, florimetry), high pressure liquid chromatography (HPLC), gel permeation chromatography (GPC), and immunassay techniques. The above described method of solubility determination is set forth more fully in *J.Pharm.Sci.*, Vol. 55, pages 1226-1227, 1966. Other methods for determining solubility include measurement of density, refractive index, electrical conductivity and the like. The details of these and other methods are described in U.S. Public Health Service Bulletin No. 67 of the Hygienic Laboratory; *Encyclopedia of Science and Technology*, Vol. 12, pages 542 to 556, 1971, published by McGraw-Hill, Inc., and the *Encyclopedic Dictionary of Physics*, Vol. 6, pages 545 to 557, 1962 published by Pergamon Press, Inc.

The porosity of the matrix, $\epsilon$, refers to the volume fraction that is permeated by the release medium and available for diffusion of the macromolecules. Various methods for determining porosity are known and can be applied to matrices of this invention. For example, $\epsilon$ can be calculated from knowledge of the tablet volume, the densities of the drug and matrix materials, and the weight percentages of all the components. Tablet volumes can be computed from tablet dimensions, and the densities of the components can be determined with an air compression pycnometer. A second method of measuring porosity consists in allowing all active agent to diffuse out of the matrix, equilibrating the empty matrix with a dilute solution of active agent of known concentration, and then permitting the active agent to be released into a known volume of fresh solvent (the same as the equilibrium vehicle). The concentration of active agent in the resulting solution is analyzed and the total amount of solute released is calculated. Analysis can be performed by any of the means described above for analysis of the solubility concentration. These two methods are described more fully by Desai, Singd, Simonelli and Higuchi, W., in *J.Pharm.Sci.*, Vol. 55, pages 1227 and 1228, 1966.

The tortuosity of the matrix, $\gamma$, is a factor which corrects for the lengthened diffusional path created by the lateral contortions of the pores. Tortuosity can be determined experimentally by measuring the release rate, Q versus $t^{\frac{1}{2}}$, per unit area of release surface of a delivery system of this invention which has been coated on all but one side with a nonpermeable material, so that the release of solute is from one planar surface. After determining the diffusivity, (A) and porosity ($\epsilon$) as described above, $\gamma$ may be calculated from the initial linear portions of the Q vs $t^{\frac{1}{2}}$ plot by means of the following equation:

$$\gamma = \frac{4\epsilon C_0^2 D}{\pi(\text{slope})^2} \qquad \text{II}$$

wherein $C_O$ is the solution concentration, and slope refers to the slope of the Q vs $t^{\frac{1}{2}}$ plot in its initial linear portion. This method is more fully described by Resai, et al in *J.Pharm.Sci.*, Vol. 55, page 1228, 1966.

It will be appreciated by those versed in the art that a major advantage of the delivery systems of this invention is the capacity to significantly vary the porosity and tortuosity of the matrix to accomodate the release of a wide variety of macromolecules. In this way, the invention provides for the programmed delivery of a macromolecular active agent.

As is shown by Equations I and II above, the release rate, Q, is proportional to both porosity ($\epsilon$) and tortuosity ($\gamma$). The $\epsilon$ and $\gamma$ parameters can be varied by raising or lowering the size of the cholesterol prills, and the ratio of cholesterol prills to cholesterol powder. The ratio of the binder to the other matrix components also has an effect on porosity and tortuosity. Generally, the larger prills and higher ratios of prills to powder will result in larger values for $\epsilon$ and smaller values for $\gamma$, i.e. greater porosity and less tortuosity. Increasing the pro-portion of binder will in general, result in the same effect.

Specific examples of how matrices can be designed to accomodate the parameters of a particular active agent and application can be had by reference to the Examples hereinbelow.

The delivery systems of this invention are easily fabricated by those skilled in the art. Generally, the active agent and the binder are first dissolved in a suitable granulating solvent, such as 50:50 ethanol water. This solution is then combined with a mixture of the cholesterol powder and cholesterol prills and mixed for a sufficient period of time to create a granulation. After complete mixing, the granulation is then passed through a stainless steel mesh screen, of mesh size 10 to 35, preferably #20. If desired, a lubricant, such as magnesium stearate, is then added and the combination is thoroughly mixed. Alternatively, the granulation may be manufactured in a fluid-based granulator-dryer such as those made by Glatt Air Technologies of Ramsey, N.J. or by Aeromatic, Inc. of Sommerville, N.J. The matrix, however made, can then be mixed with lubricant and formed into any desirable solid shape by molding, casting, pressing, extruding, drawing, or other suitable processes.

The amount of active agent incorporated in the matrix can vary between 0.1 and 10.0%, by weight, of the system, and will depend on the potency of the agent, the desired physiologic effect, the intended length of treatment, and the rate of active agent release. Preferably, the delivery systems of this invention contain about 0.5–1.5%, by weight, of active agent.

EXAMPLES

The following examples are merely illustrative of the present invention and they should not be considered as limiting the scope of the invention in any way, as the full scope of possible embodiments of the invention will become apparent to those versed in the art in light of the present disclosure and accompanying claims.

EXAMPLE 1

Growth Hormone Delivery Systems

An active agent delivery agent device comprising a matrix containing, as the active, bovine growth hormone having a molecular weight of 21,811 is manufactured as follows: First, 4.97 parts by weight (pbw) of milled crystals of bGH are mixed with 0.03 pbw of of urea, USP, and dissolved in 90:10 water:ethanol, USP. The solution is adjusted to pH 4.5 with concentrated hydrochloric acid. To this solution 0.75 pbw polyethylene glycol (PEG 6000), USP, is added and dissolved. 48 Pbw cholesterol prills having diameters of 420–707 nm, and 46 pbw cholesterol, USP, are combined and added slowly, with mixing, to the above solution. The addition of the cholesterol and subsequent mixing are performed at 40° under a nitrogen atmosphere. The resulting granulation is then passed through a 14–20 mesh screen, allowed to dry under nitrogen at 50° C., and then sifted through a 30 mesh screen. The dried and sifted granulation is blended with 0.25 pbw magnesium stearate, NF, and formed into 40 mg tablets by conventional means using ⅛" FFBE punches and dies.

Delivery systems for the controlled release of other growth hormones such as porcine (pGH) and human (hGH) are made by the above described procedure but substituting the appropriate growth hormone in place of the bovine growth hormone.

EXAMPLE 2

Insulin Delivery System 7.4 parts by weight (pbw) insulin, 0.038 pbw $NaH_2PO_4.H_2O$ and 0.062 pbw $Na_2HPO_4$ are dissolved in 60:40 water, USP:ethanol, USP. Into this solution is dissolved 2.0 pbw PEG 6000. 39 Pbw cholesterol prills having diameters of 420–707 nm are mixed with 41 pbw cholesterol USP, and added slowly, with mixing, to the above solution. Addition and mixing of the cholesterol into the solution is performed at 40° C. under nitrogen atmosphere. The resulting granulation is then passed through a 14–20 mesh screen, allowed to dry under nitrogen at 50° C., and then sifted through a 30 mesh screen. The dried and sifted granulation is blended with 0.25 pbw magnesium stearate, NF, and formed into 67–68 mg tablets by conventional means using 3/16" FFBE punches and dies.

What is claimed is:

1. A diffusional matrix delivery system for administering a macromolecular active agent at a controlled rate for a prolonged period of time to an animal body site capable of making available its intracellular and/or extracellular fluid for transfer into the system, said system comprising 90.0–99.9%, by weight, of a matrix composed of, by weight:
  (a) 20–80% cholesterol powder;
  (b) 20–80% cholesterol prills having diameters of 100–1200 microns;
  (c) 0.1–5.0% biocompatible binding agent; and
  (d) 0.1–5.0% biocompatible lubricating agent, in which is dispersed, by weight,
  (e) 0.1–10.0% macromolecular active agent,
wherein the matrix contains a plurality of micropores which are substantially permeable to the passage by diffusion of the macromolecular active agent, and said macromolecular active agent has a molecular weight between 10,000 and 400,000 and is at least ery slightly water soluble.

2. The delivery system of claim 1 wherein the matrix is composed of, by weight:
  (a) 40–60% cholesterol powder;
  (b) 40–60% cholesterol prills having diameters of 200–800 microns;
  (c) 0.1–1.0% biocompatible binding agent; and
  (d) 0.5–1.5% biocompatible lubricating agent.

3. The delivery system of claim 1 wherein the matrix is composed of, by weight:
  (a) 48–52% cholesterol powder;
  (b) 48–52% cholesterol prills having diameters of 420–710 microns;
  (c) 0.4–0.6% biocompatible binding agent; and
  (d) 0.8–1.0% biocompatible lubricating agent.

4. The delivery system of claim 1 wherein the active agent is a protein.

5. The delivery system of claim 1 wherein the active agent is a polypeptide.

6. The delivery system of claim 5 wherein the polypeptide has hormonal activity.

7. The delivery system of claim 6 wherein the active agent is a mammalian growth hormone.

8. The delivery system of claim 7 wherein the active agent is bovine growth hormone.

9. The delivery system of claim 7 wherein the active agent is porcine growth hormone.

10. The delivery system of claim 8 wherein the active agent is human growth hormone.

11. The delivery system of claim 6 wherein the active agent is insulin.

12. A method of administering a pharmaceutically acceptable macromolecular active agent to an animal at a controlled rate for a prolonged period of time which method comprises placing a delivery system shaped, sized and adapted for placement in an animal body site capable of making available its intracellular and/or extracellular fluid for transfer into the system, wherein said delivery system is a matrix which comprises, by weight:
(a) 20–80% cholesterol powder;
(b) 20–80% cholesterol prills having diameters of 100–1200 microns;
(c) 0.1–5.0% biocompatible binding agent; and
(d) 0.1–5.0% biocompatible lubricating agent, in which is dispersed, by weight:
(e) 0.1–10.0% macromolecular active agent,
wherein said matrix contains a plurality of micropores which are substantially permeable to the passage by diffusion of the macromolecular active agent, and said macromolecular active agent has a molecular weight between 10,000 and 400,000 and is at least very slightly water soluble.

13. The method of claim 12 wherein the delivery system is an implant which is sized, shaped and adapted for placement in the subcutaneous space of a warm-blooded animal.

14. The method of claim 13 wherein the active agent is a member selected from the group consisting of bovine growth hormone, porcine growth hormone, human growth hormone and insulin.

15. The method of claim 12 wherein the delivery system is an implant which is sized, shaped and adapted for placement in the intraperitoneal space of a warm-blooded animal.

16. The method of claim 12 wherein the delivery system is an implant which is sized, shaped and adapted for placement in the eye.

17. The method of claim 12 wherein the delivery system is an insert which is sized, shaped, and adapted for placement in the eye.

18. The method of claim 12 wherein the delivery system is an insert which is sized, shaped and adapted for placement in the vagina.

19. The method of claim 12 wherein the delivery system is an insert sized, shaped and adapted for placement in the uterus.

20. The method of claim 12 wherein the delivery system is an insert which is sized, shaped and adapted for placement in the anus.

21. The method of claim 12 wherein the delivery system is an insert sized, shaped and adapted for placement in the nasal passages.

* * * * *